US00PP19060P3

(12) United States Plant Patent
Howe

(10) Patent No.: US PP19,060 P3
(45) Date of Patent: Aug. 5, 2008

(54) ***SEDUM PURPUREUM* 'PINK CHABLIS'**

(50) Latin Name: *Sedum spectabile*
Varietal Denomination: Pink Chablis

(75) Inventor: Christopher B. Howe, Nunica, MI (US)

(73) Assignee: Hortech, Inc., Spring Lake, MI (US)

( * ) Notice: Subject to any disclaimer, the term of this patent is extended or adjusted under 35 U.S.C. 154(b) by 855 days.

(21) Appl. No.: 09/514,930

(22) Filed: Oct. 15, 2001

(65) Prior Publication Data

US 2004/0216198 P1 Oct. 28, 2004

(51) Int. Cl.
*A01H 5/00* (2006.01)

(52) U.S. Cl. ..... Plt./263

(58) Field of Classification Search ..... Plt./263, Plt./226

See application file for complete search history.

*Primary Examiner*—Kent Bell
(74) *Attorney, Agent, or Firm*—Penny J. Aguirre

(57) ABSTRACT

A showy *Sedum* cultivated variety (cultivar) named 'Pink Chablis', characterized by white and blue-green variegated leaves, compact habit, and pink fall borne flowers.

4 Drawing Sheets

Latin name of the genus and species of the plant claimed: 'Pink Chablis' is claimed to be a cultivar of the genus *Sedum* and species *spectabile*.

Variety denomination: 'Pink Chablis'.

BACKGROUND OF INVENTION

'Pink Chablis' originated in Nunica, Mich. as a naturally occurring branch sport (mutation) of the unpatented cultivar *Sedum spectabile* 'Brilliant' (not patented). The parent plant of *S. spectabile* 'Brilliant' was growing in a nursery setting (Hortech) in a 1 gallon size container. Christopher Howe noticed the branch sport mutation (containing variegated leaves and later named 'Pink Chablis') during the course of his duties as an employee of Hortech. The cultivar 'Brilliant' typically displays blue-green leaves, green flower buds, and deep purplish pink flower petals on rounded inflorescences. 'Pink Chablis' differs in having its blue green leaves edged in creamy white. Furthermore, its flower buds are white, and its flower petals are light pink. It is similar to the parent cultivar only in habit (shape) of the plant.

The first successful asexual reproduction of 'Pink Chablis' was carried out by its discoverer, Christopher Howe. This propagation took place under controlled conditions in Nunica, Mich., on Jun. 15, 1995. The mutated branch was excised and consisted of four sets of leaves and a stem. It was cut (with a knife) and prepared into two cuttings each containing two sets of leaves. These were treated with 3000 ppm IBA, and rooted under intermittent mist over a period of two weeks. Two cuttings rooted and were transplanted to separate one-gallon size pots for further growing.

SUMMARY OF INVENTION

Once the plants rooted in to the one-gallon pots and matured, a process that typically takes one full growing season, they were planted out in the landscape where they displayed blue green leaves that were edged in creamy white. In August white flower buds were formed in broad flat-topped panicles. By September, the flower buds had opened to reveal petals of clear pink. The overall habit of the plants were similar to the parent cultivar. Mature plants reach approximately 1½ feet tall (measured from soil to top of foliage plane) and approximately 20 inches tall when in flower (measured from soil to top of plane of the inflorescences). Mature plants display a width of approximately 2 feet across.

On Feb. 28, 1996 international registration as an herbaceous plant cultivar was applied for. The international registrar at the International Plant Union in Freising Germany approved the application for registration on Mar. 22, 1996.

BRIEF DESCRIPTION OF THE VARIOUS VIEWS OF THE DRAWINGS

The accompanying photographic illustrations show typical foliage of the cultivar and the closest known comparison plant (the unpatented cultivar *Sedum* 'Frosty Morn') with color being as accurate as possible with renditions of this type. The photographs were taken at 1:00 P.M. Jul. 1, 1999 (foliage depictions) and Sep. 1, 1999 (floral depictions) under cloudy conditions, in Nunica, Mich. The film used was Fujifilm ISO 200 exposed for 1/30 second at F8 using no filters.

FIG. 1 depicts a top perspective view of 'Pink Chablis'.

FIG. 2 depicts flowers and foliage of 'Pink Chablis'.

FIG. 3 depicts plants of the comparison cultivar 'Frosty Morn'.

FIG. 4 depicts a side perspective view of the comparison cultivar 'Frosty Morn'.

DETAILED BOTANICAL DESCRIPTION

'Pink Chablis' has not been observed under all possible environmental conditions, and the phenotype may vary significantly with variations in environment, such as temperature, light intensity and day length. The following observations, measurements, and comparisons describe this plant as grown in Nunica, Mich. when container grown (outdoors without cover) in conditions that approximate those generally used in commercial practice.

The following traits have been repeatedly observed and are determined to be the basic characteristics of 'Pink Chablis', which in combination distinguish this showy *sedum* as a new and distinct cultivar. The plants described were 3 years old and grown in the ground in full sun conditions in Nunica, Mich. The color codes correspond to The Royal Horticultural Society Color Chart. The following description is based upon a four year-old plant that is mature in every respect.

1. Succulent deciduous foliage is simple, oppositely arranged and sometimes whorled. In youth, the foliage is obovate in outline, 1 inch long, ½ inch wide, irregularly toothed above the middle, hairless, tacky to the touch, and colored light-green 129-C. Immature leaves bear the same colors on their upper and lower surfaces. Leaf margins are colored green white 157-A above and below, 1/16 inch to 3/16 inch wide. Leaves sessile. Juvenile leaf apexes obtuse, bases broady cunneate.
2. In maturity, the foliage is obovate in outline, hairless, 3-3½ inches long, 1½-2 inches wide. Mature leaves bear the same colors on their upper and lower leaves. Leaf blades are colored green 129-A with slender irregular areas of lighter green 129-C. Irregularly toothed leaf margins are ⅛ inch to ⅜ inch wide, colored green white 157A, ⅛ inch to ⅜ inch wide. Leaves sessile. Apices obtuse, bases broadly cuneate.
3. The midvein is light green 130-C and is only slightly raised above the blade. It gives rise to smaller and equally visible secondary veins of the same color.
4. Stems are herbaceous and arise vertically from a clump. Typically they are erectly oriented, sometimes arching. Stems reach 14 to 18 inches in length, and mature to ½ inch wide. The stems are round in cross section and range from ¼ to ⅜ inch wide. In youth and in maturity they are colored green 128-D.
5. Internodes range in length from 1 to 1½ inches.
6. Bisexual flowers are borne in August. Flower buds are ovate with sharp terminal point, 3/16 in. long, ⅛ in. wide, and colored white 155-D. During September, they open to reveal pink, 64C, petals (same color top and bottom). Petals are 1/16 inch wide and ⅙ inch long and ovate shaped. Their apexes are acute, bases connate, and margins smooth. Individual flowers last approximately one month, are 5-parted, and reach ¼ inch wide.
7. Flowers are densely set and arranged in compound cymes, which reach 5 to 6½ inches wide in maturity. Each inflorescence is held at a height of approximately 20 inches above the ground. Each carries 500-750 flowers. Flowers exude a mild sweet fragrance. Flowers are with five red-purple 74-A pistils ¼ to ⅜ inch in length, five red-purple 74-A stamens ¼ to ⅜ inch in length, and 5 white 155-D sepals (same color top and bottom). Sepals are 1/32 inch wide and 1/16 inch long and ovate or lanceolate. Their apexes are acute and bases connate, and margins smooth.
8. Peduncles range from ¾ to 1¼ in. long, ⅛ in. wide, green 192-B. Pedicles range from approximately ⅜ to 7/18 in. long, 1/16 in. wide, colored green 192-B.
9. Carpels erect and pale pink 49-D, stigmas 1/16 inch wide red purple 67-B, styles 1/32 in. wide and ⅛ in. tall colored red-purple 62-D, and ovaries 1/10 in. diameter colored 62-D. Red-purple 72-B pollen is sparsely produced.
10. Aggregate fruit is 1/16 inch to 2/16 inch in length, 1/32 to 2/32 inch wide at the base rising to a pointed tip.
11. Mature plants typically display broad, compact, mounded habit. Maximum observed height is 18 inches (prior to blooming) and maximum observed width is 24 inches.

Other cultivars of *Sedum spectabile* include 'Frosty Morn', which is not patented and differs in having more slender curled leaves orientated at 45 degree angles from the stems. The branches of 'Frosty Morn' exceed 24 inches. The flowers of 'Frosty Morn' are less dense and uniform. The panicles are 3 to 4 inches wide with 10-20 forked branches.

Propagation is successfully achieved spring through summer by stem cuttings. Plants are successfully propagated by crown division year around. Plants produced by these methods remain true to type. No resistance or unusual susceptibility to common diseases and pests of this host have, to date, been observed or verified. Winter hardiness is reliable in USDA Zone 4B through 7B.

I claim:

1. A new and distinct showy *Sedum spectabile* plant named 'Pink Chablis', as illustrated and described.

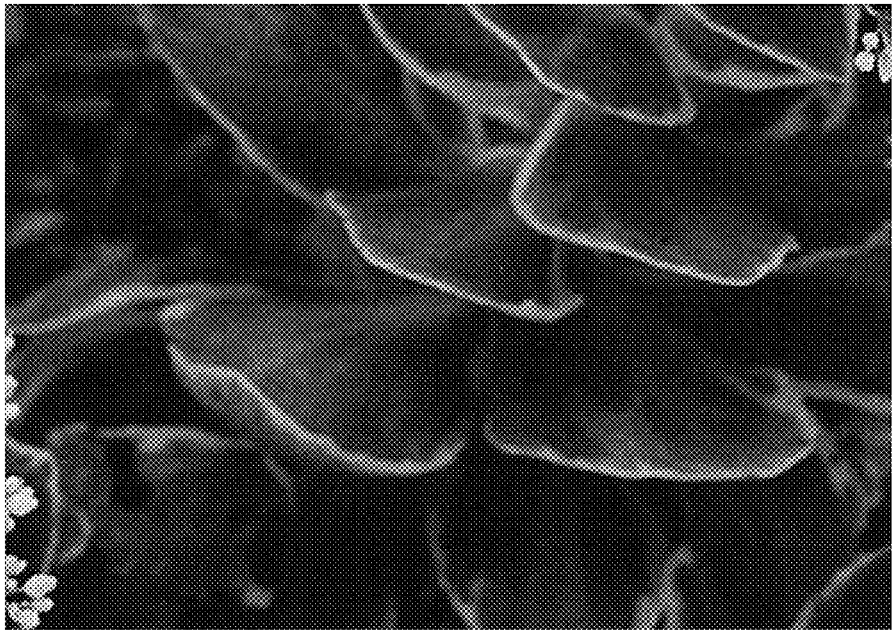

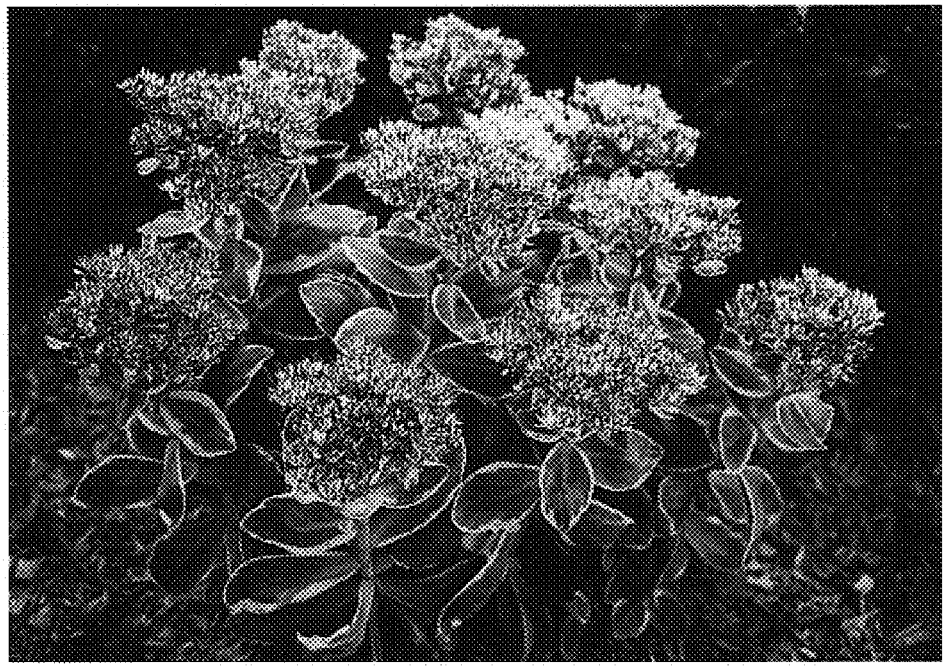

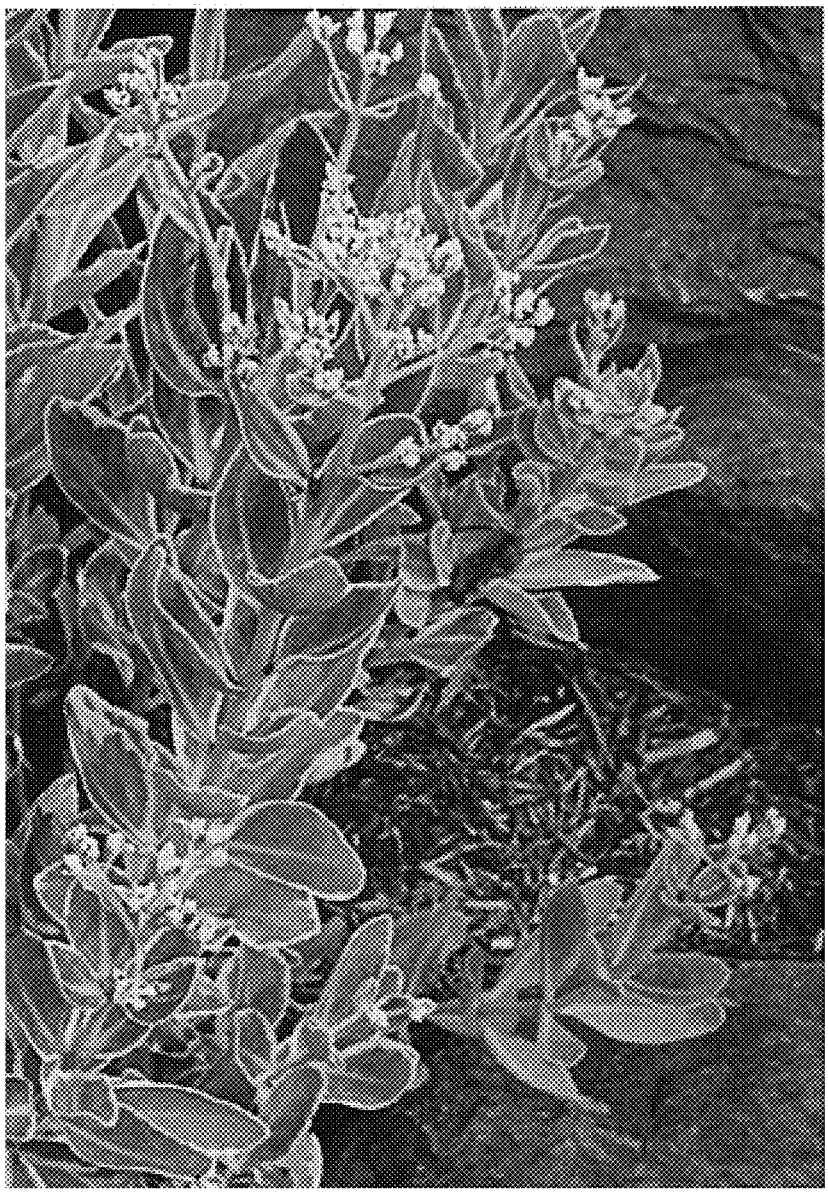

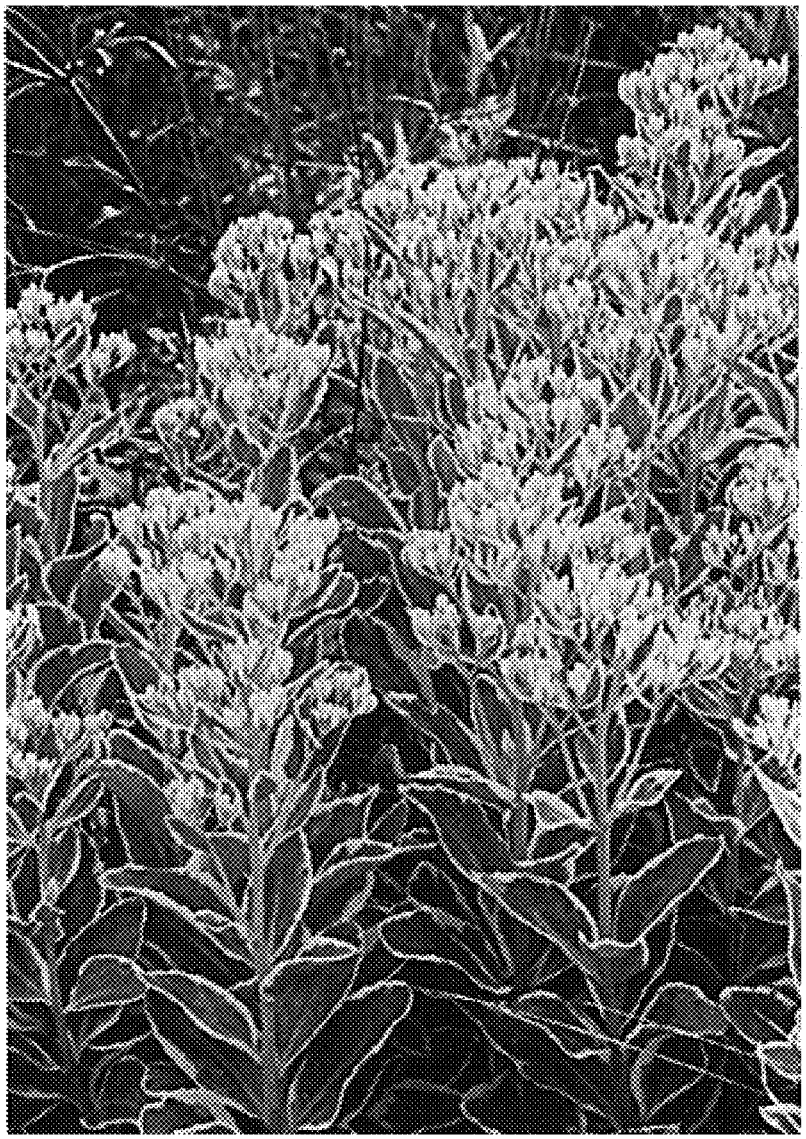

* * * * *